United States Patent
Kwon et al.

(10) Patent No.: US 6,718,820 B2
(45) Date of Patent: Apr. 13, 2004

(54) APPARATUS FOR INDENTATION TEST AND METHOD FOR MEASURING MECHANICAL PROPERTIES USING IT

(75) Inventors: Dong-il Kwon, Kangnam APT. #6-306, Bangbae 3-dong, Seocho-gu, Seoul (KR); Yeol Choi, Seoul (KR); Yun-hee Lee, Kyeongsangbuk-do (KR)

(73) Assignees: Frontics, Inc. (KR); Dong-il Kwon (KR)

( * ) Notice: Subject to any disclaimer, the term of this patent is extended or adjusted under 35 U.S.C. 154(b) by 0 days.

(21) Appl. No.: 10/209,237

(22) Filed: Jul. 31, 2002

(65) Prior Publication Data
US 2004/0020276 A1 Feb. 5, 2004

(51) Int. Cl.⁷ .................................. G01N 3/48
(52) U.S. Cl. ............... 73/81; 73/82; 73/83; 73/85; 73/87
(58) Field of Search .................. 73/81, 82, 83, 73/84, 85, 86, 87

(56) References Cited

U.S. PATENT DOCUMENTS

| | | | | |
|---|---|---|---|---|
| 3,738,160 A | * | 6/1973 | Sobajima | 73/81 |
| 4,061,020 A | * | 12/1977 | Fridley et al. | 73/81 |
| 4,852,397 A | | 8/1989 | Haggag | 73/82 |
| 5,062,293 A | * | 11/1991 | Bakirov et al. | 73/81 |
| 6,516,655 B1 | * | 2/2003 | Adrian | 73/83 |

* cited by examiner

Primary Examiner—Hezron Williams
Assistant Examiner—David Rogers
(74) Attorney, Agent, or Firm—Hayes Soloway P.C.

(57) ABSTRACT

The present invention relates to an apparatus for indentation test, for measuring mechanical properties in the field. The present invention provides an apparatus which is suitable for measuring mechanical properties without compensative experimental constant for the analysis of measured data. The present invention provides an apparatus which is safe for testing the materials by utilizing a sensor for controlling indenter movement.

8 Claims, 13 Drawing Sheets

APPARATUS FOR INDENTATION TEST AND METHOD FOR MEASURING MECHANICAL PROPERTIES USING IT

TECHNICAL FIELD

The present invention relates generally to an apparatus for indentation test, and more particularly to an apparatus for the continuous indentation test for evaluating mechanical properties of the materials such as tensile properties in the field by analyzing the data measured by the test.

BACKGROUND OF THE INVENTION

Mechanical properties of the materials used for industrial structures/facilities are declined as time passes at the environmental condition of high pressure and temperature. It is necessary to develop non-destructive testing method to find out the degradation of the mechanical properties of the materials to evaluate the structural integrity of the materials used. This means that an apparatus for measuring mechanical properties of materials in the field (exterior to a testing laboratory) is needed. The apparatus for indentation test for evaluating mechanical properties by analyzing indentation load-displacement curve from measured load and displacement data is invented for this purpose.

There is a patent entitled "Field indentation microprobe (FIM) for structural integrity evaluation(U.S. Pat. No. 4,852, 397)" in the field of indentation test. But this invention requires the extra test to compensate experimental constant for the analysis of measured data. So, this invention needs extra cost and it is difficult to get mechanical property data of the materials if standard specimen is not acquired. Therefore, there is a need to provide an apparatus which is used for measuring the mechanical properties of materials without need of standard specimen.

Also, there is a need to provide an apparatus for indentation test which is applicable to materials irrespective of size or kinds.

Also, there is a need to provide an apparatus for indentation test which is efficiently movable according to the testing positions of materials.

Therefore, it is an object of the present invention to provide an apparatus for measuring method of mechanical properties without compensating experimental constant for the analysis of measured data, thus extra standard test is not necessary.

It is another object of the present invention to provide an apparatus that is applicable to materials irrespective of size or kinds by diversifying attaching means for indentation test.

It is also another object of the present invention to provide an apparatus which is appropriate for testing multiple positions of the materials by adopting a horizontal moving means.

It is further another object of the present invention to provide an apparatus which is safe for testing the materials by utilizing a sensing means for controlling indenter movement.

BRIEF SUMMARY OF THE INVENTION

The present invention relates to an apparatus for indentation test for measuring the mechanical properties of materials in the field.

In the present invention, there is provided an apparatus which is applicable to materials irrespective of size or kinds by diversifying attaching means for indentation test.

The apparatus in accordance with the present invention is suitable for testing multiple positions of materials by adopting a horizontal moving means.

The present invention provides an apparatus which is suitable for performing a method of measuring mechanical properties without compensating experimental constant for the analysis of measured data.

The present invention provides an apparatus which is safe for testing the materials by utilizing a sensing means for controlling indenter movement.

BRIEF DESCRIPTION OF THE DRAWINGS

FIG. 12 is a flow curve (stress v. strain) derived from indentation load-displacement curve of FIG. 11a.

DETAILED DESCRIPTION OF THE PRESENT INVENTION

Figure 1:
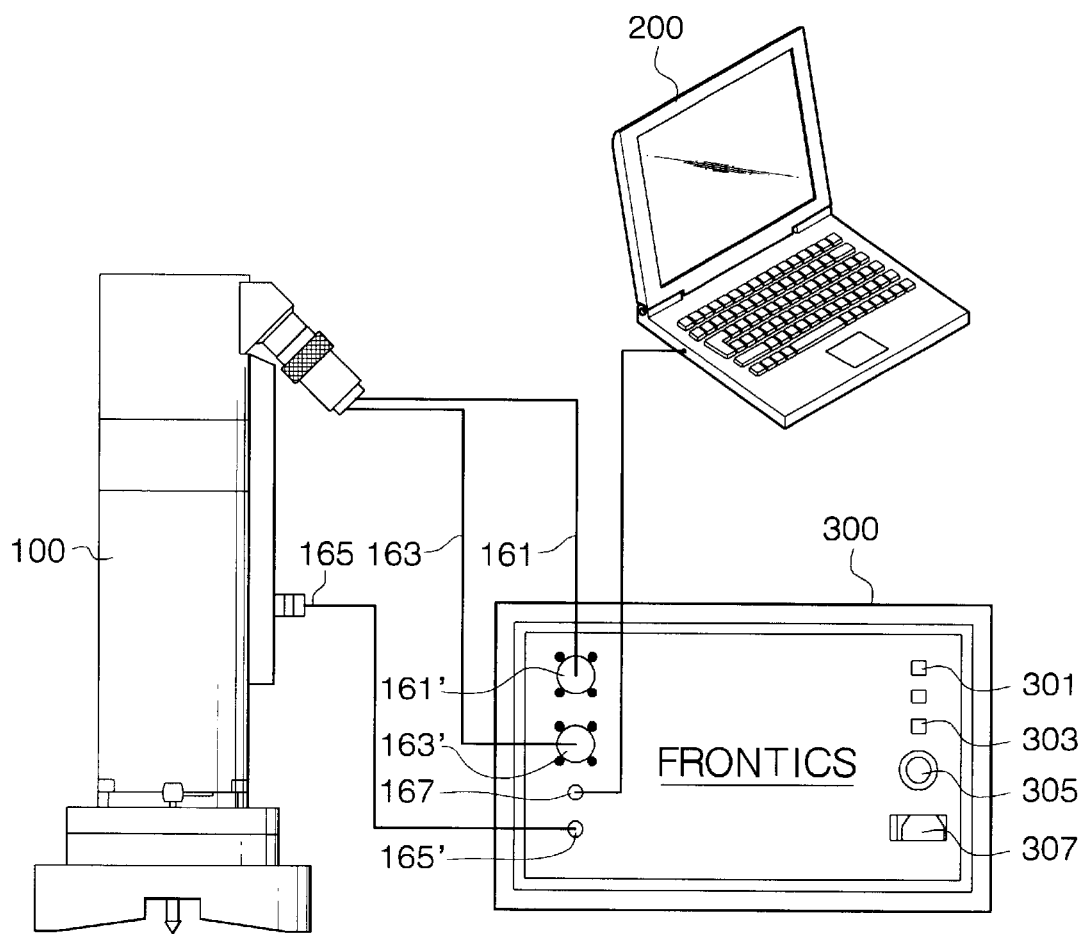
FIG. 1 is a schematic drawing illustrating the apparatus according to an embodiment of the present invention.

The present invention provides an apparatus for indentation test, which measures load and displacement of test materials and comprises (i) a load applying means that has a load generating motor, a reduction gear, a coupling and a connecting axis; (ii) a load delivery means that transforms rotary power generated by the load applying means to a vertical load; (iii) a load sensing means attached to the load delivery means for measuring load; (iv) an extension axis; (v) an indenting means for applying contact load to the test materials comprising an indenter holder and an indenter which is exposed at the end of the indenter holder; and (vi) a displacement sensing means that measures displacement of the test materials.

Also, the present invention provides an apparatus for indentation test, having the space for the connecting axis and the indenter holder to move vertically, which further includes a main body base for supporting the components (hereinafter collectively 'main body') below the main body, and an attaching means that is connected to the main body base to fix the apparatus for indentation test into test materials. As the attaching means, a magnet, a chain or a U-block may be used.

Also, the present invention provides an apparatus for indentation test which further includes a horizontal moving means that moves a main body including the indenter in one horizontal direction while a main body base and an attaching means are fixed. The horizontal moving means has a slider base which has dovetail in upper surface and is connected to the main body base at the upper surface of the main body base, a slider which is positioned between the slider base and the main body and has dovetail groove for attaching to the dovetail of slider base at the lower surface and screw groove made at the outer surface in the same direction with the dovetail groove, and a moving handle which has two ends, of which one end is screwed with screw pitch of the groove of slider and the other end has a handle, and is screwed with the main body base or the slider base by bracket.

Also, the present invention provides an apparatus for indentation test which further includes a sensing means for controlling indenter movement that sets up the limitation of the movement of indenter for safety.

Also, the present invention provides an apparatus for indentation test in which the indenter is ball type, cone shape or square-pyramid shape. And the indenter holder and the indenter are in one united body.

The present invention provides an apparatus for indentation test in which the predetermined load is from 0.2 kgf to 2 kgf and the predetermined distance is from 5 $\mu$m to 30 $\mu$m.

Also, the present invention provides an apparatus for indentation test which further includes a programming means connected to said main body for instructing a step of approaching an indenting means to a starting point to said test materials, a step of load applying to set up a predetermined loading rate and a predetermined indentation displacement, then to apply said indentation load to said test materials, a step of load removing for said indenting means to move vertically upward according to a unloading ratio, a step of measuring indentation load and indentation displacement during load applying and load removing, a step of repeating cycle of measuring indentation load and indentation displacement during repeated load applying and load removing cycle, a step of removing said indenting means from test materials, and a step of drawing a indentation load-displacement curve derived from the measured data.

Embodiments of the present invention will be described in detail referring to the drawings. These embodiments are only examples of the present invention in order to explain the technological ideas of the present invention, and the present invention is not limited by the embodiments.

1. The Apparatus for Indentation Test

Referring to FIG. 1 through FIG. 5, an embodiment of the indentation apparatus in accordance with the present invention is explained.

Figure 2:
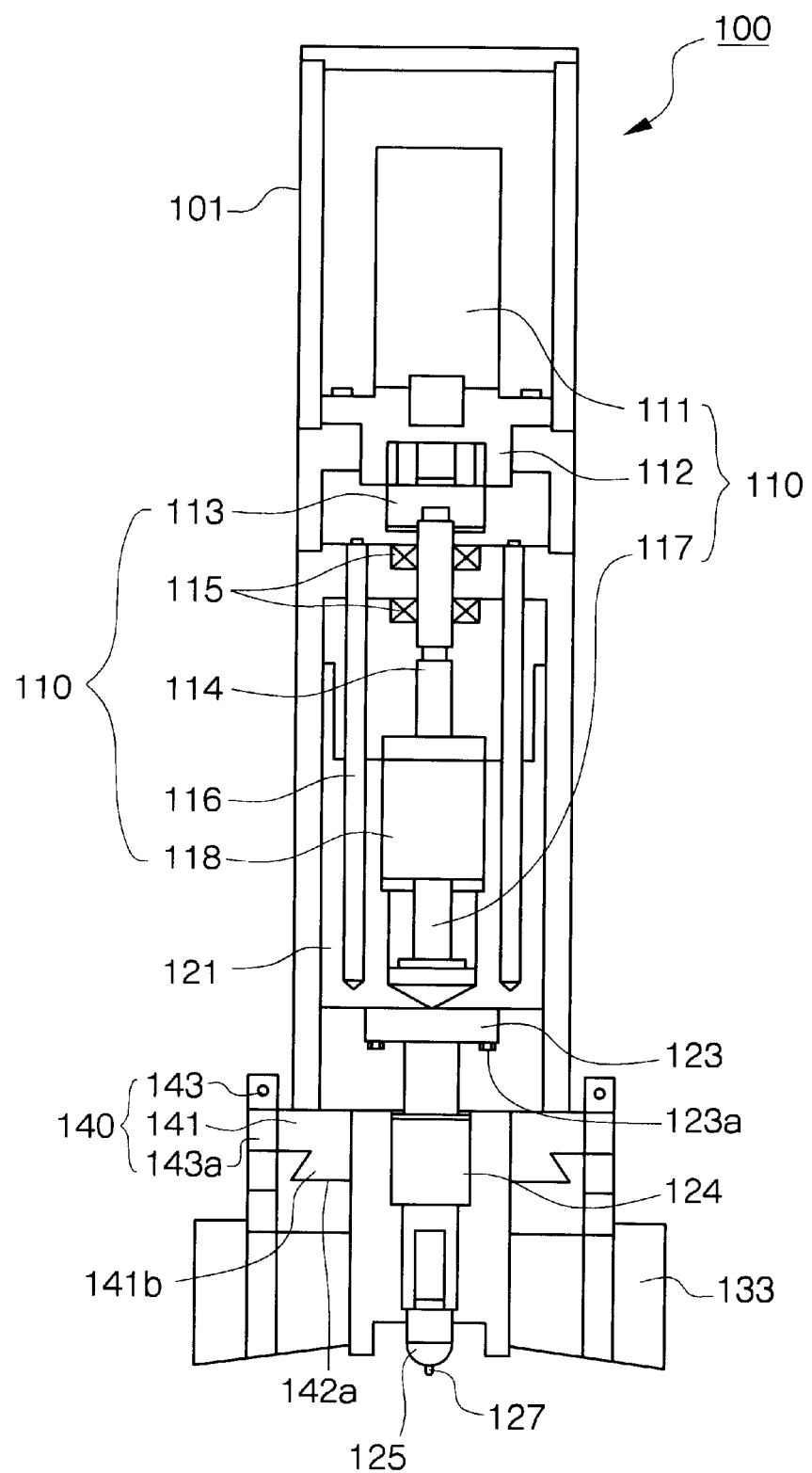
FIG. 2 is a front cross-sectional view of the main body of FIG. 1.
Figure 3:
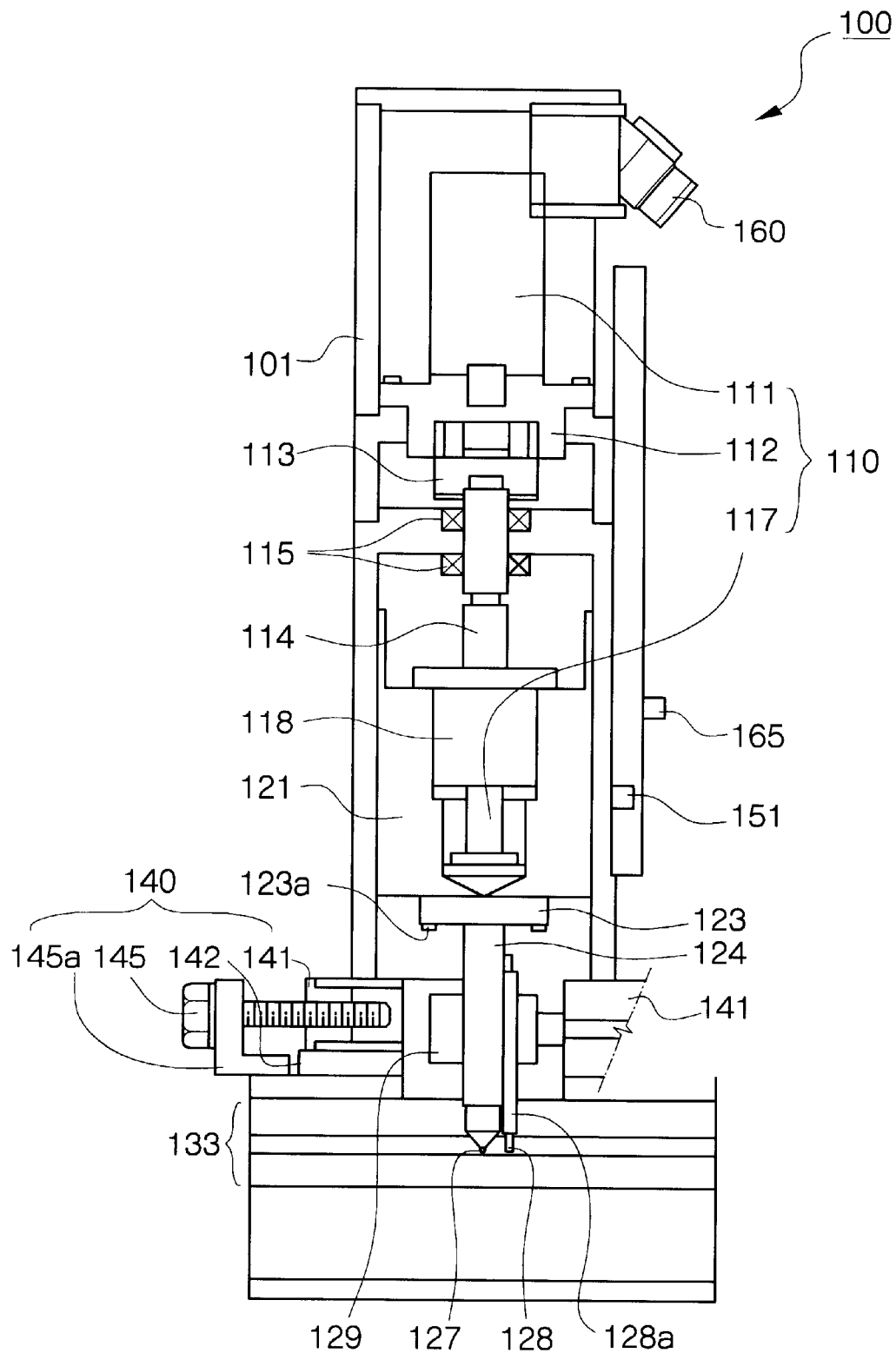
FIG. 3 is a side cross-sectional view of the main body of FIG. 1.
Figure 4:
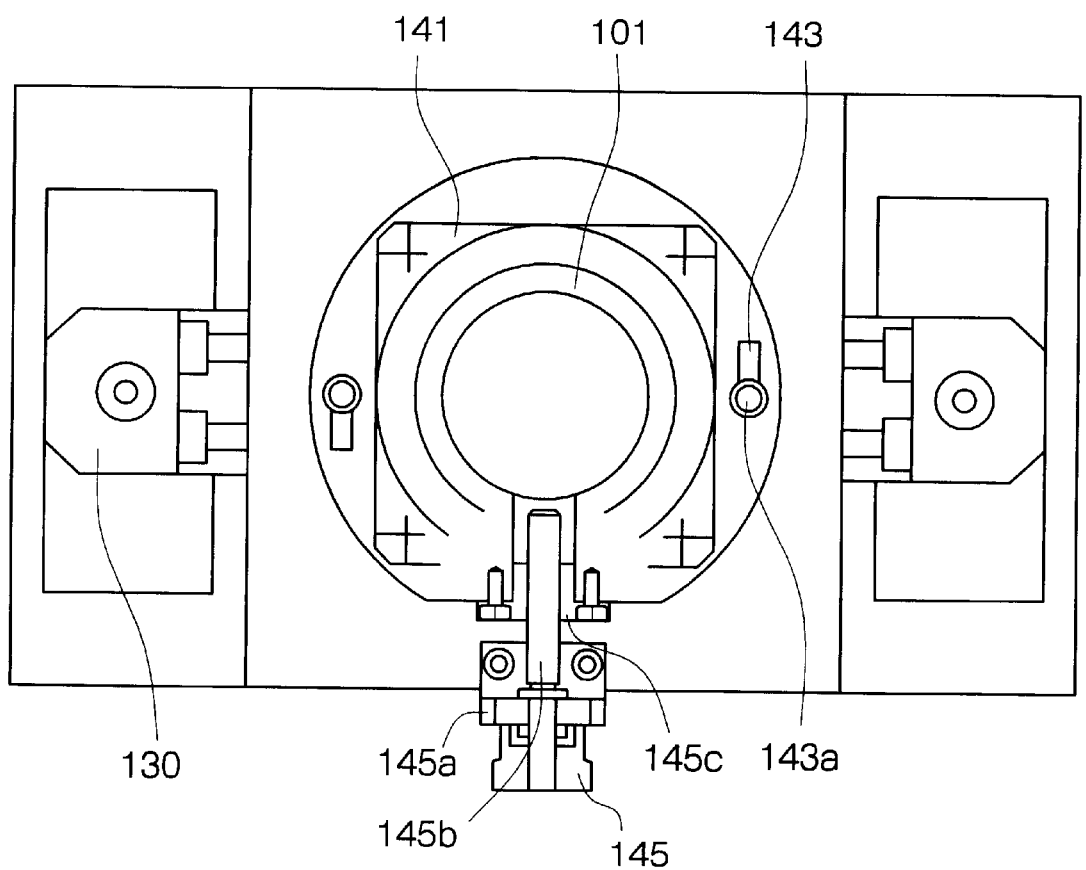
FIG. 4 is a plane view including a part of cross-sectional view of the horizontal moving means of FIG. 1.
Figure 5:
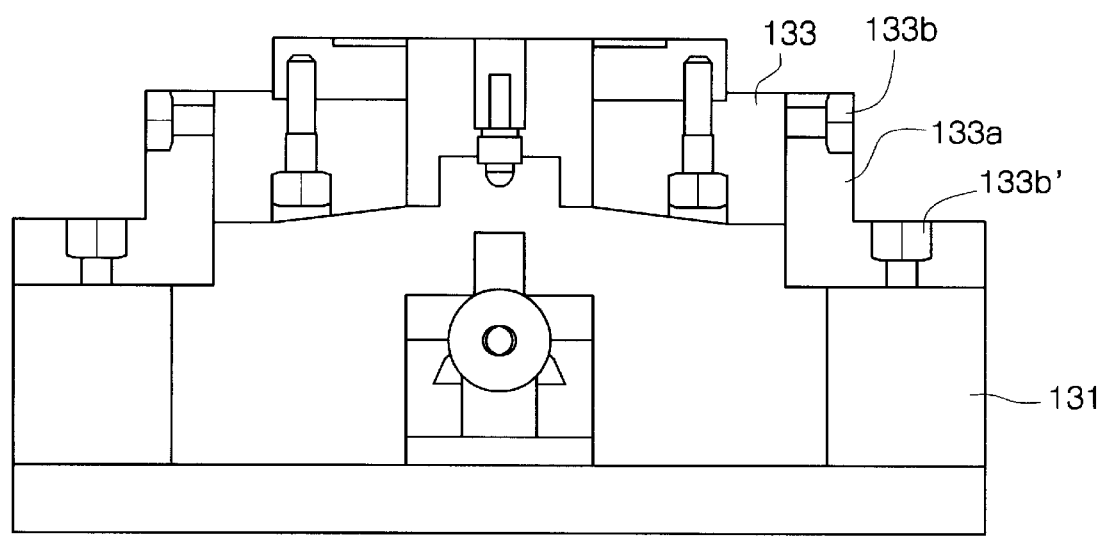
FIG. 5 is a cross-sectional view of the lower part of the main body, attaching means and specimen table of FIG. 1.

FIG. 1 is a schematic drawing illustrating the apparatus according to an embodiment of the present invention. FIG. 2 is a front cross-sectional view of the main body of FIG. 1. FIG. 3 is a side cross-sectional view of the main body of FIG. 1. FIG. 4 is a plane view including a part of cross-sectional view of the horizontal moving means of FIG. 1. FIG. 5 is a cross-sectional view of the lower part of the main body, attaching means and specimen table of FIG. 1.

Referring to FIG. 1, the apparatus according to the present invention basically includes a main body 100, a computer 200 connected to the main body 100 and an interface board 300 which connects the main body 100 to the computer 200.

The main body 100 is the main part of the apparatus for performing the indentation tests which is attached to test materials. The computer 200 controls the main body 100 and contains the program to analyze the data measured by the main body 100. The interface board 300 is the means to convert the signals between the main body 100 and the notebook computer 200. The connectors included in the main body 100 and the notebook computer 200 are connected to the connectors of the interface board 300.

Referring to FIG. 2 and FIG. 3, the main body includes a frame 101, a load applying means 110, a cylinder (a load delivery means) 121, a load sensing means 123, an indenter holder 125, an indenter 127, a displacement sensing means 128, a sensing means for controlling indenter movement 151 and a connector of the main body 165.

The frame 101 is a cylindrical case to protect the inner components. The frame 101 includes the load applying means 110, the cylinder (load delivery means) 121, the load sensing means 123 and a part of the indenter 127. It is easy to carry the frame 101 because it is made of ultra-light aluminum alloy.

The load applying means 110 comprises a motor 111, a reduction gear 112 and a ball screw 117. The motor 111 is an AC servo motor which is stable for overloading and is controlled precisely, and thus eliminates the effects of outside parameters in the field such as vibration. The reduction gear 112 is located below the motor 111, and reduces the speed of the indenter 127 suitable for the tests by reducing the power transported to the indenter 127. A coupling 113 located below the reduction gear 112 connects the connecting axis 114 to the reduction gear 112, and transports the power generated by the motor 111 to the connecting axis 114. The bearings 115 located around the connecting axis 114 supports the rotation movement of the connecting axis 114. The supporting axis 116 penetrating the cylinder 121 guides the movement of the cylinder 121, prevents the vibration of the cylinder 121, and protects the cylinder 121 from the vibration when the cylinder 121 moves up and down. The ball screw 117 is rotated by the power generated by the motor 111, and applies the load to the load sensing means 123. The ball screw nut 118 is combined with the ball screw 117 using the screw pitch. Thus, the ball screws nut 118 moves up and down vertically when the ball screws 117 rotates.

The cylinder 121 converts the rotary power generated by the load applying means 110 to a vertical load in order that the indenter 127 may apply the vertical load to test materials. The cylinder 121 is compressively combined with the ball screw nut 118. The cylinder 121 is penetrated by the supporting axis 116 as explained above.

The load sensing means 123 located below the cylinder 121 is connected with the cylinder 121 by a screw 123a, and measures the load applied by the cylinder 121. When the load sensing means 123 is indented, the deformation proportional to the applied load makes the resistance of deformation gauge in the load sensing means 123 changed, and finally the applied load can be measured by measuring the changed current. The maximum capacity of the load sensing means 123 is 300 kgf and the load resolution is 0.3 kgf. Because the excessive maximum capacity of the load sensing means 123 makes it difficult to precisely analyze the data and the insufficient maximum capacity makes it difficult to obtain enough data, it is necessary to determine the optimum maximum capacity by the various experiments.

The extension axis 124 is located below the load sensing means 123. The male screw at the upper end of the extension axis 124 is combined with the female screw at the lower end of the load sensing means 123.

The indenter holder 125 and the indenter 127 are located at the end of the extension axis. The indenter 127 applies contact load to the test materials. The indenter holder 125 and the indenter 127 are combined in one unit (collectively called an indenting means). As the indenter holder 125 and the indenter 127 composes one unit, the separation of the indenter 127 from the indenter holder 125 caused by damage of the indenter holder 125 can be avoided and the experimental error caused by division of the indenter holder 125 and the indenter 127 can also be avoided. The indenter 127 is a type of spherical, cone or square-pyramid according to applications. In certain circumstances, the indenter holder 125 and the indenter 127 can be divided.

The displacement sensing means 128 is located below a connector 128a contacted with the indenter 127 in parallel. The displacement sensing means 128 can be inserted into inside groove formed at the lower end of connector 128a when force is applied. And it can be restored to initial position by elastic material that is installed in inside groove when force is removed. A sensor bracket 129 attaches the extension axis 124 which is connected to the indenting means to the connector 128a which is connected to the displacement sensing means 128. When the indenter 127 indents the test material, the displacement sensing means 128 is inserted into the inside groove of the connector 128a. The depth of the insertion equals the indentation depth of the indenter 127, and so the indentation depth of the indenter 127 can be measured. The maximum measurable displacement of the displacement sensing means 128 is 2 mm and LVDT (Linear Variable Displacement Transducer) is used for measuring the accurate indentation depth.

The horizontal moving means 140 is located between the load sensing means 123 and a main body base 133. The horizontal moving means 140 is used for moving the main body 100 including the indenting means horizontally for conducting another indentation test in another position of the test material while the main body base and the attaching means are fixed.

Referring to FIG. 2, FIG. 3 and mainly FIG. 4, the horizontal moving means 140 which is located below the frame 101 of main body 100 is composed of a slider 141, a slider base 142, a locking means 143, a locking means volt 143a and a moving handle 145. The slider 141 is located below the frame 101 of main body 100 and the slider base 142 is located below the slider 141. Depressive dovetail groove (not shown) is formed in the slider base 142 and prominent dovetail (not shown) is formed in the slider 141. Both are fitted to each other. Therefore, the slider 141 can slide along with the dovetail 141b (or the dovetail groove 142a) direction on the slider base 142 and make the main body 100 move horizontally. The locking means volt 143a is cross-sectionally contacted with the slide base 142 through the groove formed in the slider 141. As the locking means 143 is associated with the locking means volt 143a, rotation of the locking means 143 makes the locking means volt 143a move up and down. When the locking means 143 is rotated for extension of the locking means volt 143a, it presses the slider base 142 to fix the slider 141. In this state, when the locking means 143 is rotated for shortening of the locking means volt 143a, it releases the pressure to the slider base 142 and makes the slider 141 move horizontally when force is applied to the slider 141. The moving handle 145 generates the force making the slider 141 move horizontally. There is nut 145c which is formed in the slider 141 through the bracket 145 combined with volt 145b. As the moving handle 145 is rotated, the volt of the moving handle 145b is also rotated. The rotation of the volt of the moving handle 145b makes the nut of the moving handle 145c, the slider 141 and the frame 101 move to the direction or opposite direction of the moving handle 145 along with the direction of screw pitch. There are indicators showing that the distance of movement is formed on the moving handle 145.

A sensing means for controlling indenter movement 151 is attached to avoid the damage to apparatus, which results from excessive upward or downward movement of the indenter 127 and the displacement sensing means 128. After the limit regions where the indenter 127 and the displacement sensing means 128 can move safely are defined, the sensing means for controlling indenter moving 151 is attached at the boundary of the limit regions respectively. When the movement of the indenter 127 and the displacement sensing means 128 are out of the safe regions, the rotation of motor is stopped and thereafter the movement of the indenter 127 and the displacement sensor 128 are also stopped.

A main body base 133 is located below the main body 100. The main body base 133 connects an attaching means 130 with the main body 100 or supports the main body 100 when the attaching means 130 is not installed.

Referring to FIG. 5, the apparatus for indentation test is composed of the main body 100 and also attaching means 130. The attaching means 130 consists of magnet 131, magnetic bracket 131a and two volts 133b, 133b'. The magnetic bracket 131a and the two volts 133b, 133b', connect the magnet 131 and the main body base 133 by screws. The magnet 131 is used when object to which the apparatus is attached is iron and steel type material. The magnet 131 is used as a rounded form fitted to curvature in case the tested materials have curvature. Chain and U-block are also used along with the tested materials to which the apparatus is attached. Chain is used for wrapping the tested materials for attachment when the magnet 131 cannot be used. 4-Lined chain is used for supporting large load up to 300 kg and it is connected to the main body base 133 by volts or screws. When U-block is used, brackets of both sides are connected to U-block by volts to support the main body 100.

Referring to FIG. 1, main body connector that is located at the top of the main body's frame 101 makes the main body 100 communicate with interface board 300. The main body connector consists of a motor connector 161, an encoder connector 163 and a displacement connector 165, which are connected with motor connector 161', encoder connector 163' and displacement connector 165' of interface board 300, respectively.

Mechanical properties of materials such as hardness, flow curve, yield strength, work hardening index, tensile strength, non-uniform strain etc. can be obtained in the field by computer in which a program analyzing indentation load applied to the test materials and displacement data is embedded. The calculating methods are described in Korean Patent Application Nos. 2001-1770 (The calculating method of work hardening index and stress coefficient using continuous indentation test), 2001-1771 (The calculating method of yield using continuous indentation test) and 2001-1772 (The calculating method of tensile strength using continuous indentation test).

Also the program embedded in computer includes manual driving function for the indenter approaching to the tested material or for the indenter withdrawing from the tested material and engage function for the indenter to make an automatic initial positioning.

Referring to FIG. 1, motor connector 161', encoder connector 163' and displacement connector 165', which are connected with motor connector 161, encoder connector 163 and displacement connector 165 of main body respectively, are located in interface board 300. Also computer connector 167 which is connected with communication port of notebook computer 200, UP/DOWN button 301 for manual movement of the indenter 127 upward or downward, an initializing button 303, an emergency button 305 and a power button 307 are located in interface board 300.

Referring to FIGS. 1, 2, 3, 4 and 5, operation of the apparatus in accordance with the invention is explained in detail as follows.

After the attaching means 130 is combined with main body base 133 by screws, the attaching means 130 is attached to the testing material. Locking means 143 is rotated to move locking volt 143a down to press slider base 142 for fixing of slider 141 and main body 100. Pushing power button 307 of interface board 300 makes motor 111 be rotated by program embedded in notebook computer and then reduction gear reduces the velocity which is suitable for the indenter 127 movement. Rotational force of motor 111 rotates connecting axis 114 and the ball screw 117 and makes the ball screw nut 118 move down vertically. The vertical movement of the ball screw nut 118 makes the cylinder 121, the load sensing means 123, the extension axis 124, the indenter holder 125 and the indenter 127 move down simultaneously. At this time the load sensing means 123 measures the change of load constantly. The indenter 127 indents into the tested material. When the indentation depth increases by indentation of the indenter 127, the displacement sensing means 128 is inserted into the groove of the connector 128a. The distance of insertion equals the indentation depth. The procedure of obtaining data of stress and strain by measuring load and the indentation depth upon gradual removing of load applied to the indenter 127 by load sensing means 123 and the displacement sensing means 128 is performed at one position. Repeating of the procedures mentioned above can complete stress-stain curve at one position.

The same indentation test is performed in another test position after moving slider 141 horizontally by releasing the locking means 143 of horizontal moving means 140 and rotating moving handle 145.

Magnet can be formed in a curved form to be attached to the object that has a curvature. If magnet is not appropriate, other attaching means such as a chain and a U-block can be used. After rotating volt 133b which connects magnetic bracket 133a of attaching means 130 to the main body base 133 by screws to separate the attaching means 130 from the main body 100, other attaching means can be used.

2. The Method of Measuring Data and Calculating Mechanical Properties Using the Apparatus for Indentation Test The method of measuring data and calculating mechanical properties using the apparatus for indentation test is explained with reference to FIG. 6 through FIG. 8. FIG. 1 through FIG. 5 are also considered.

Figure 6:
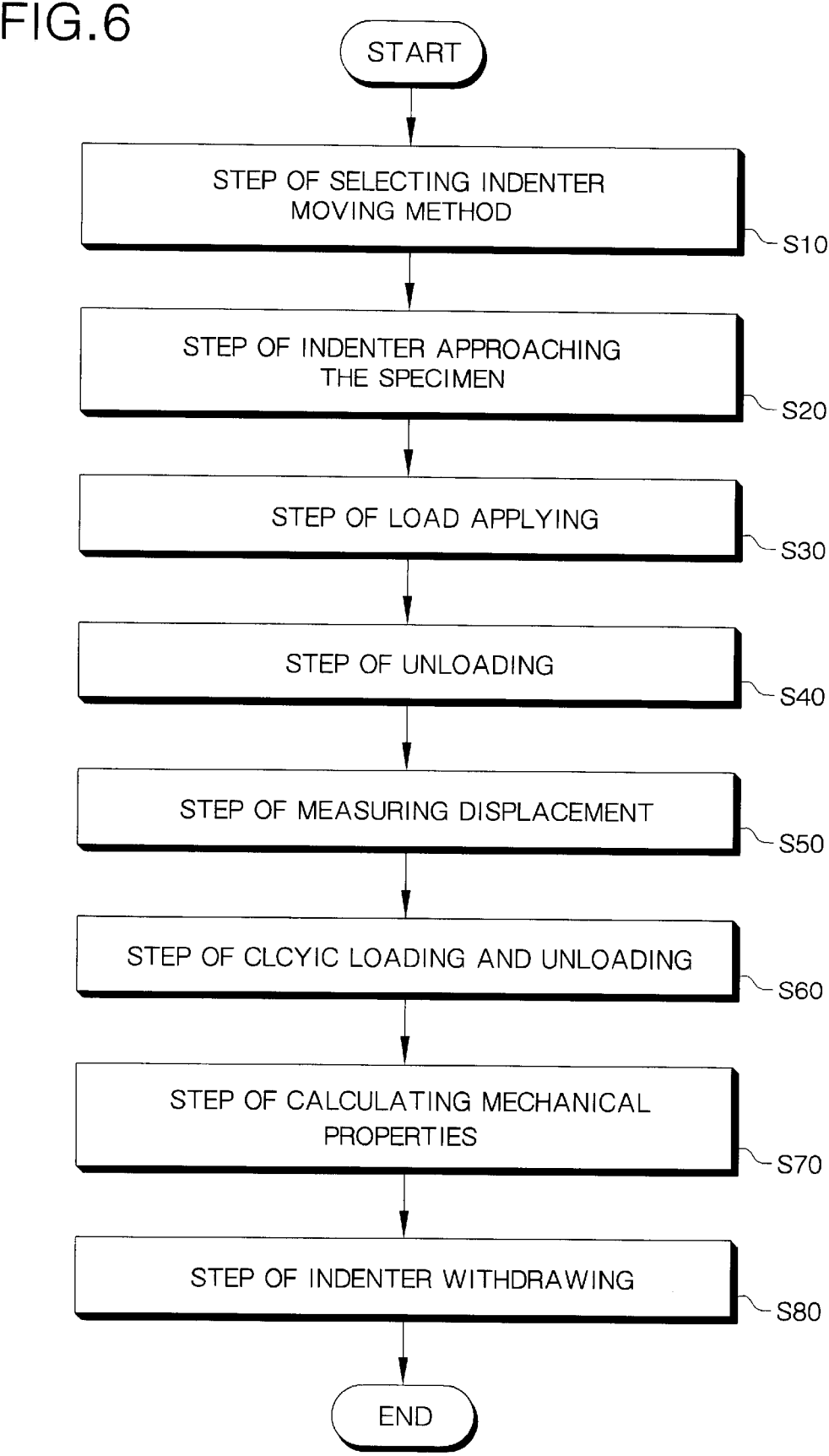
FIG. 6 is a flow chart of a method for measuring mechanical properties according to an embodiment of the present invention.
Figure 7:
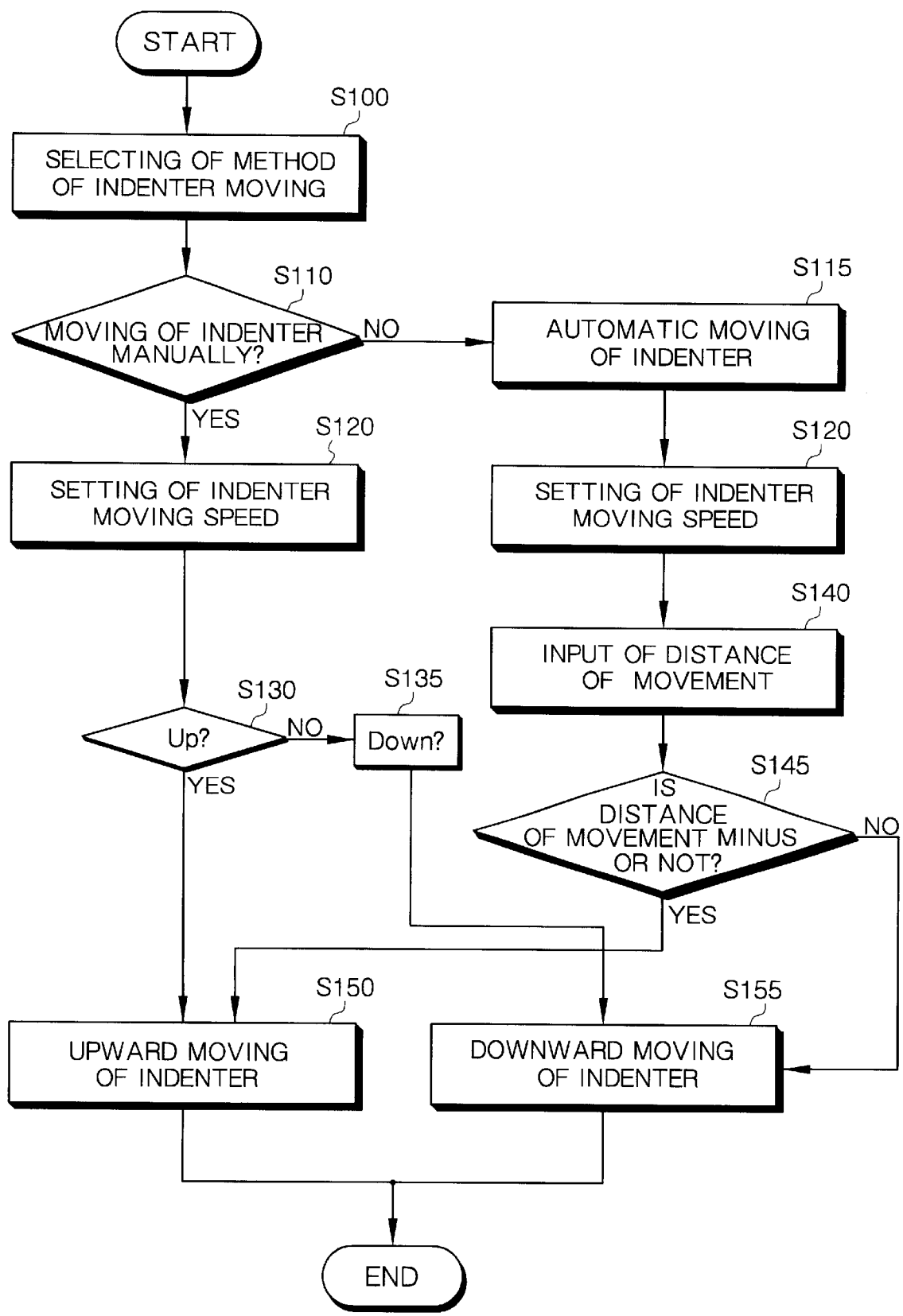
FIG. 7 is a flow chart of the step for selecting a method of indenter moving of FIG. 6.
Figure 8:
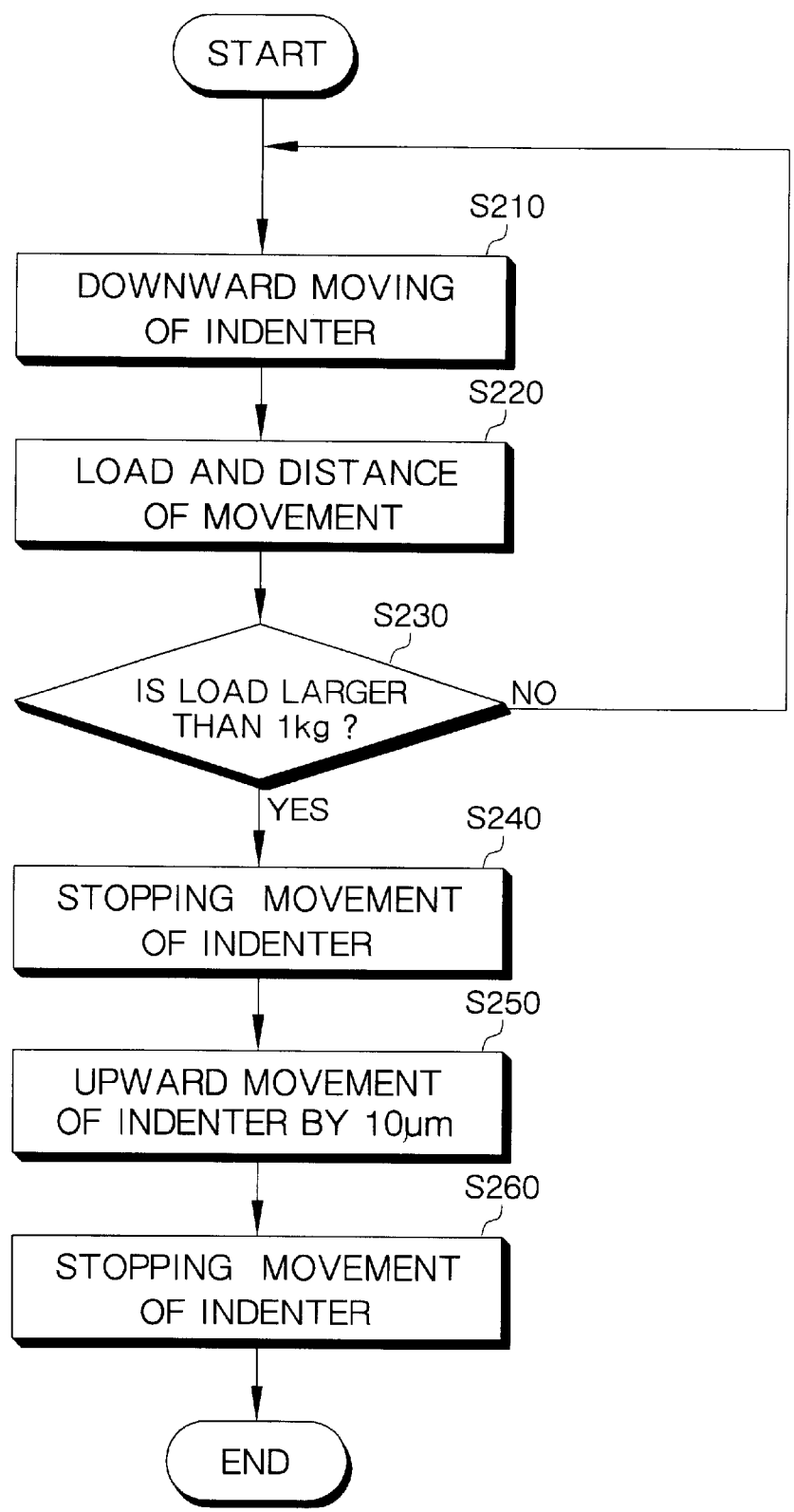
FIG. 8 is a flow chart of the step for indenter approaching the specimen of FIG. 6.

FIG. 6 is a flow chart of a method for measuring mechanical properties according to an embodiment of the present invention. FIG. 7 is a flow chart of the step for selecting indenter moving method of FIG. 6. FIG. 8 is a flow chart of the step for indenter approaching the specimen of FIG. 6.

Referring to FIG. 6, a method for measuring mechanical properties using the apparatus for indentation test according to the present invention comprises a step of selecting indenter moving method(S10), a step of indenter approaching the specimen(sample material)(S20), a step of load applying(S30), a step of unloading(S40), a step of measuring displacement(S50), a step of cyclic loading and unloading (S60), a step of calculating mechanical properties(S70), and a step of indenter withdrawing(S80).

A step of selecting indenter moving method(S10) is selecting whether to move an indenter 127 automatically or move manually. Referring to FIG. 7, selection of indenter 127 moving method is performed to make an indenter approach a sample, before indentation test gets started(S10). Analysis program asks whether to move an indenter manually and if yes, then loading rate is determined(S120). Then, touching an Up button(S130) makes an indenter move upward(S150) and touching a Down button(S135) makes an indenter move downward(S155).

In case of selecting automatic moving(S115), after loading rate is set up(S120'), moving distance(S140) is inputted. If moving distance is minus, the indenter is moved upward (S150) and if moving distance is positive, the indenter is moved downward(S155).

A step of indenter approaching the specimen(S20) is approaching an indenter 127 to the test materials. Referring to FIG. 8, displacement and load are indicated(S220) at real time during the indenter is moved downward(S210). Then if the load on the indenter is over 1 kgf(YES), downward moving of the indenter is stopped(S240) and moved 10 μm upward(S250) and stopped(S260). If the load on the indenter is under 1 kgf(NO), the indenter is moved downward until the load reaches 1 kgf and repeats the step for indenter approaching the specimen. The 1 kgf and 10 μm are the predetermined value of load and displacement, respectively, obtained from experiment. The load and displacement values are available in the range between 0.2~2 kgf, 5~30 μm respectively. A step of load applying(S30) is loading indenter on the materials. The moving rate and the moving displacement are predetermined. The rate and displacement are controlled by a motor 111 and a reduction gear of the apparatus. For example, in case that maximum displacement is 300 μm and the number of sequence is 10, the rate can be 0.1 mm/min and the displacement for one movement is 30 μm.

A step of unloading(S40) is moving the indenter upward by removing the load to a specific ratio. This process is also controlled by a motor 111 and a reduction gear of the apparatus. If the unloading ratio is 30%, the indenter is moved upward to the load of 70% of the initial load.

A step of measuring(S50) is measuring the indentation displacement and indentation load of the indenter 127 during the step of load applying(S30) and the step of unloading (S40). This step(S50) is performed by a displacement sensing means 128 and a load sensing means 123.

A step of cyclic loading and unloading(S60) is repeating the step of load applying(S30) and the step of unloading (S40) to a specific number of times. The moving rate, moving displacement, and unloading ratio are predetermined differently at each sequence.

A step of calculating mechanical properties(S70) is as follows. Stress-strain curve is derived from indentation load—indentation displacement curve obtained in measuring step (S50). And mechanical properties are calculated using this stress-strain curve. Here, properties are flow curve, yield strength, strain-hardening exponent, tensile strength, Luders strain, etc. The calculating methods are described in Korean Patent Application Nos. 2001-1770 (The calculating method of work hardening index and stress coefficient using continuous indentation test), 2001-1771 (The calculating method of yield using continuous indentation test) and 2001-1772 (The calculating method of tensile strength using continuous indentation test).

A step of indenter withdrawing(S80) is withdrawing the indenter 127 from materials. A step of calculating mechanical properties(S70) can be positioned before or after indenter withdrawing step(S80).

Using the horizontal moving means 140, the indenter 127 can be moved to the direction of one axis horizontally. By repeating the measuring sequence to the same materials, mechanical properties of the same materials can be obtained several times. With excluding too large or too small data from the results, averaging the rest data can acquire more precise mechanical properties.

3. The Programming Means Storing a Method of Measuring Mechanical Properties Using the Apparatus for Indentation Test.

The programming means storing the method of measuring mechanical properties using the apparatus for indentation test(hereinafter, referred to as 'programming means') is explained with reference to FIG. 9 through FIG. 12. A computer 200 can operate the programming means. For example, the programming means operated by the computer 200 in FIG. 1 controls the apparatus through the interface board 300, and calculates mechanical properties of materials based on data measured by the apparatus.

Figure 9:
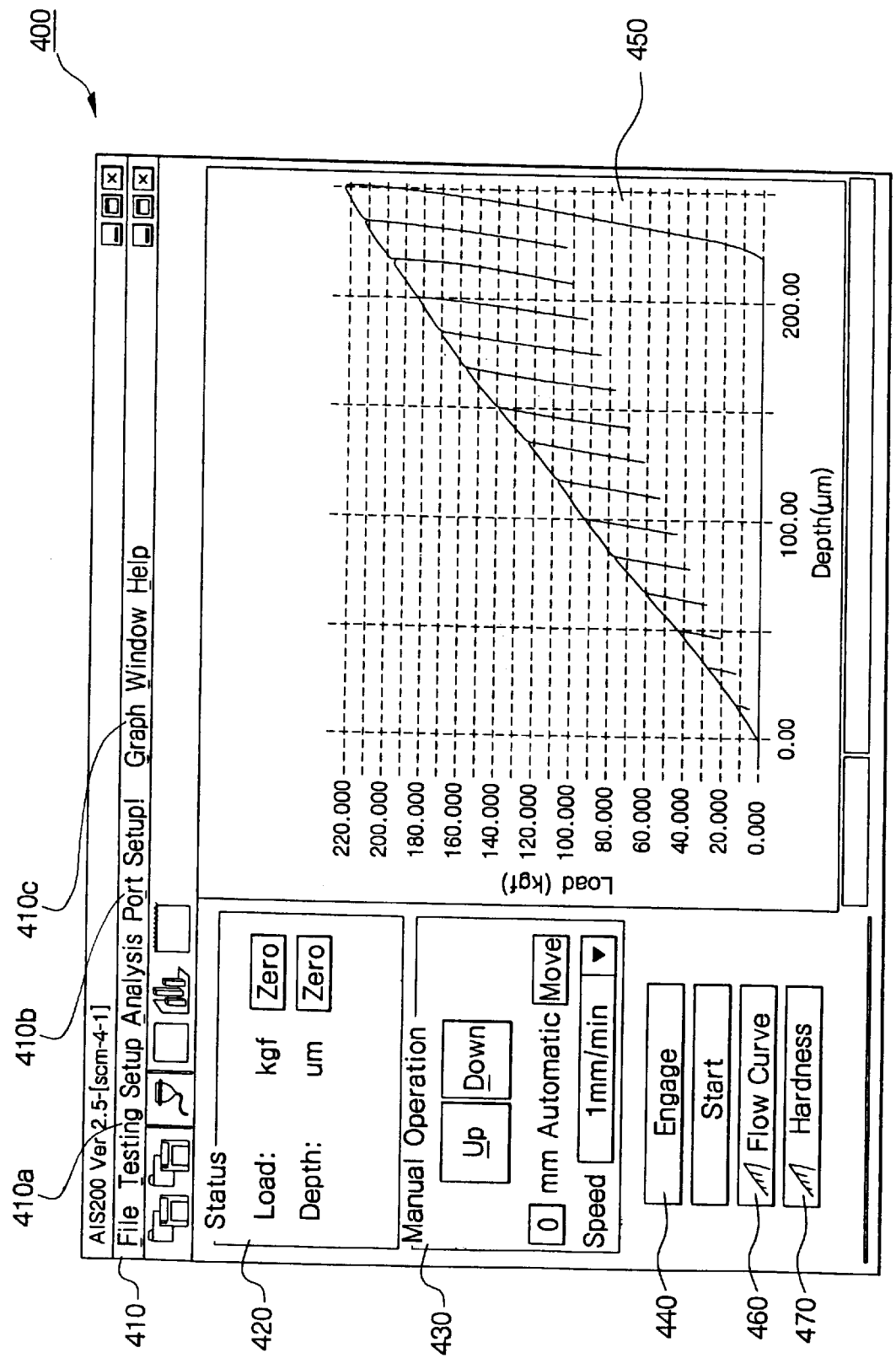
FIG. 9 is an initial picture of programming means storing a method for measuring mechanical properties using the apparatus for indentation test according to the present invention.
Figure 10:
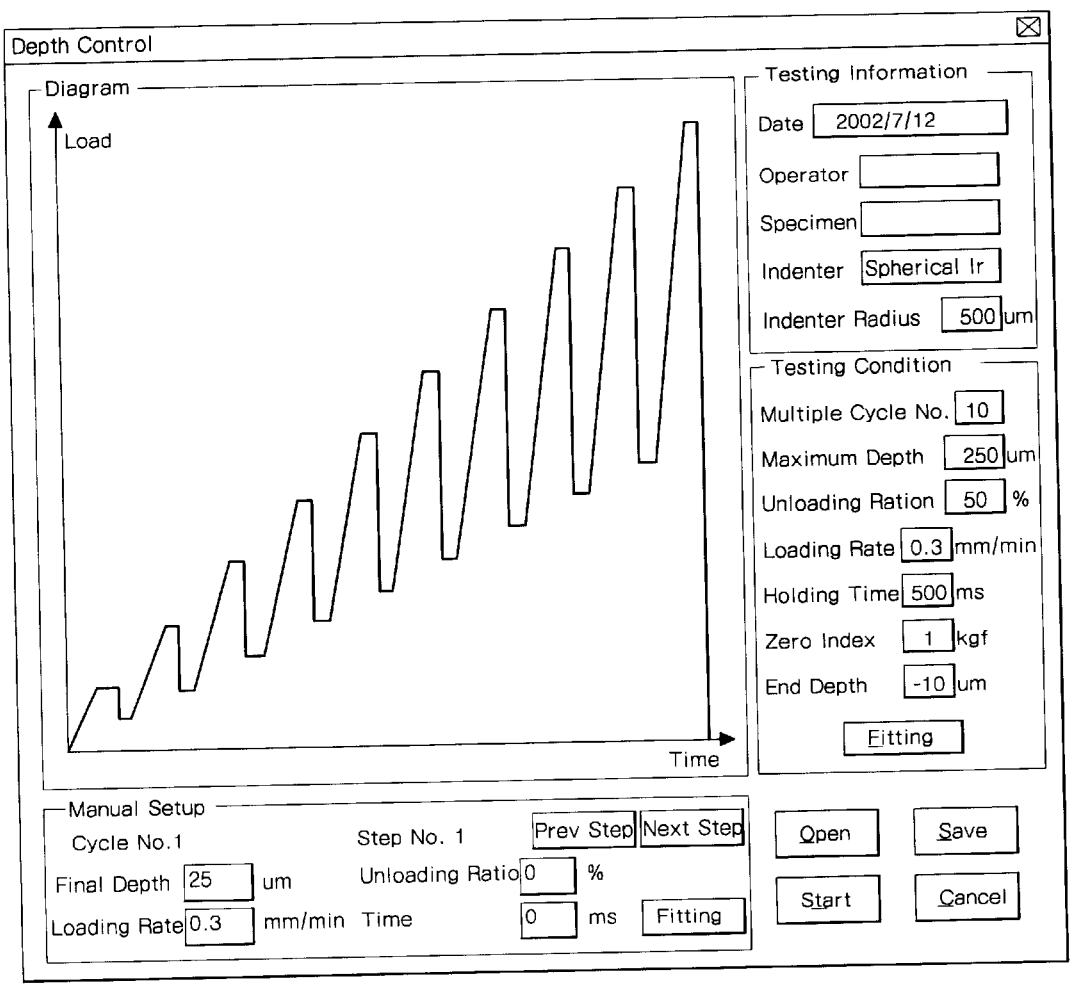
FIG. 10 is a picture of setting up the experiment condition of FIG. 9.
Figure 11A:
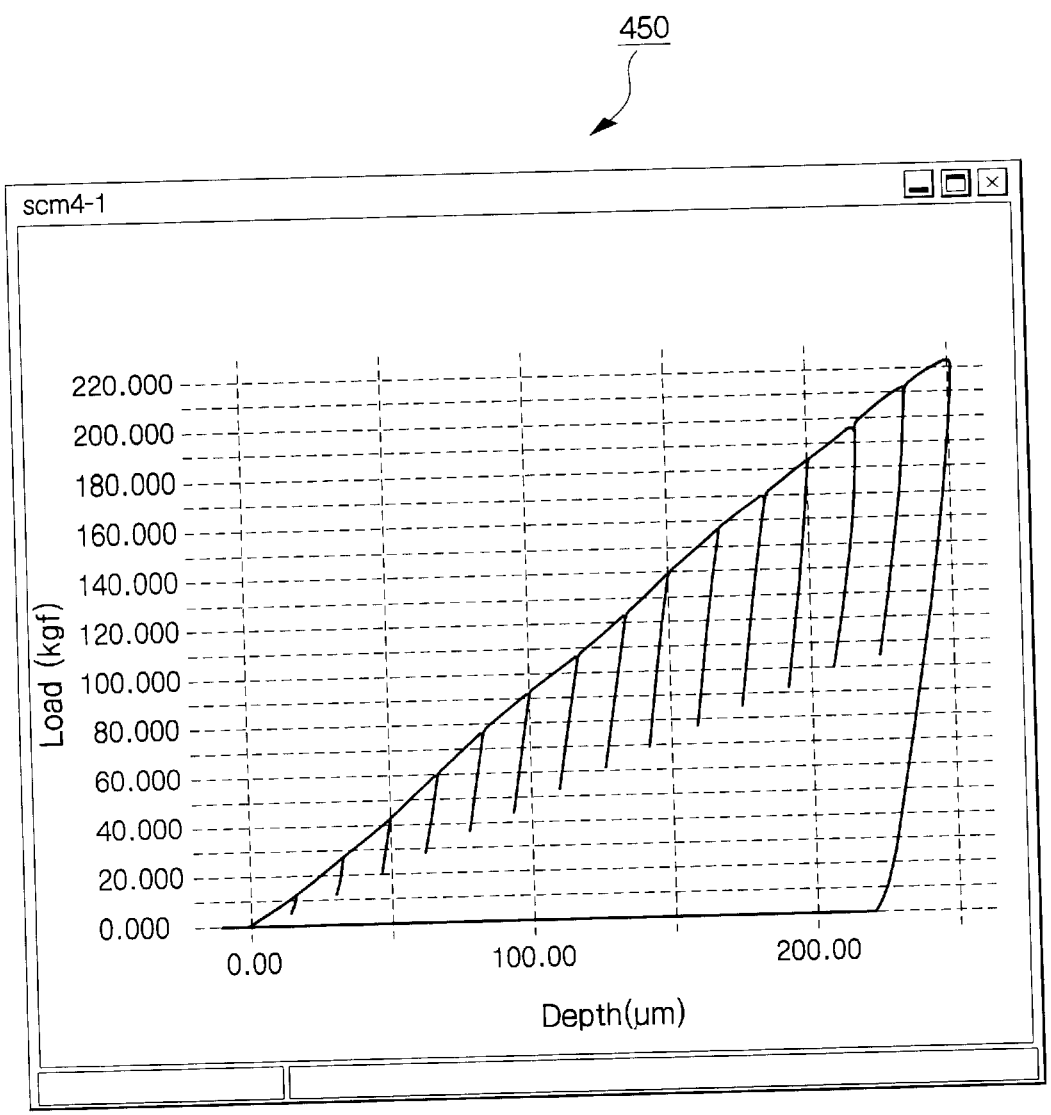
FIG. 11a is a picture of indentation load-displacement curve derived from the data measured by the apparatus for indentation test according to an embodiment of the present invention.
Figure 11B:
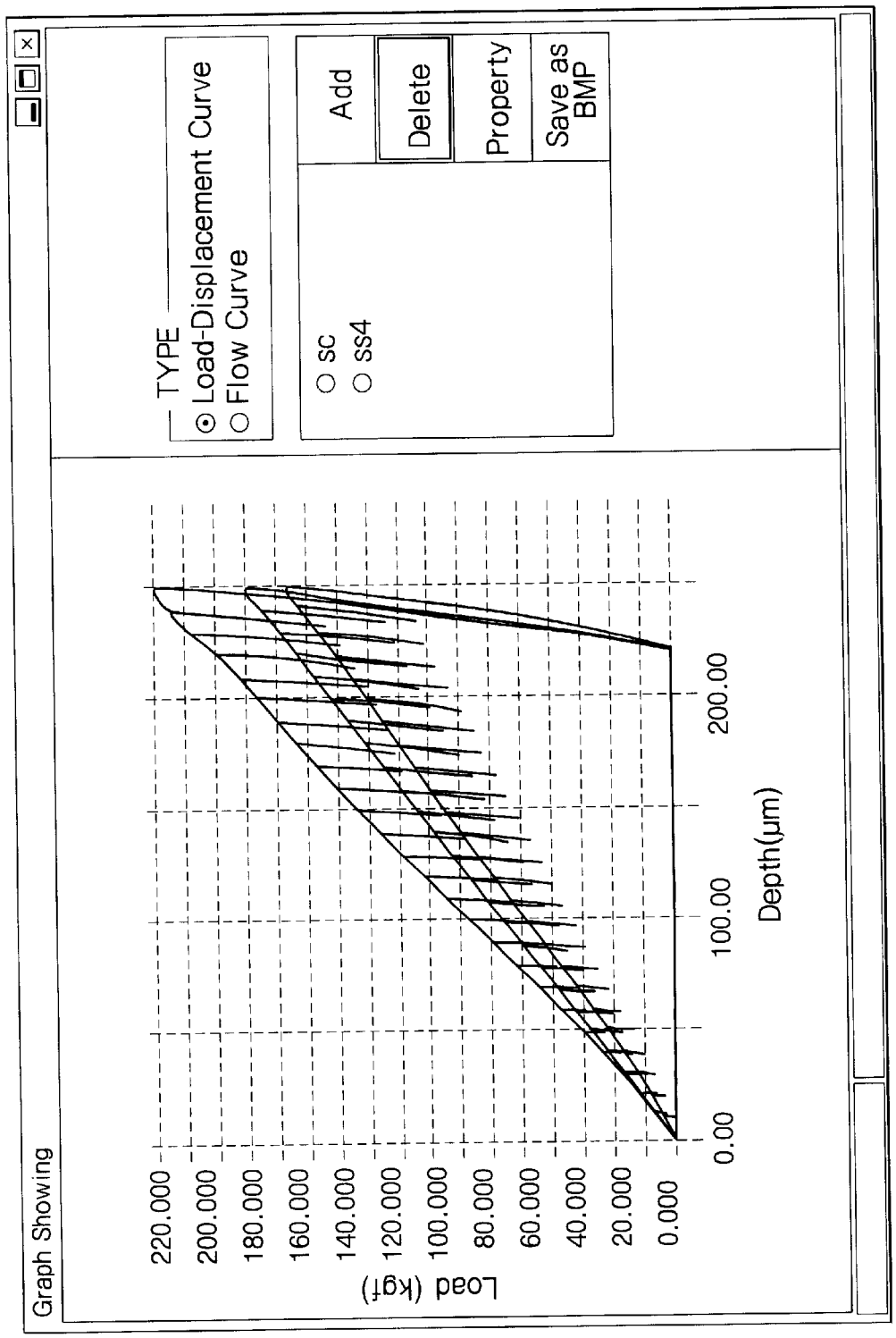
FIG. 11b is a picture of indentation load-displacement curves derived from the data measured by a number of testing of materials.
Figure 12:
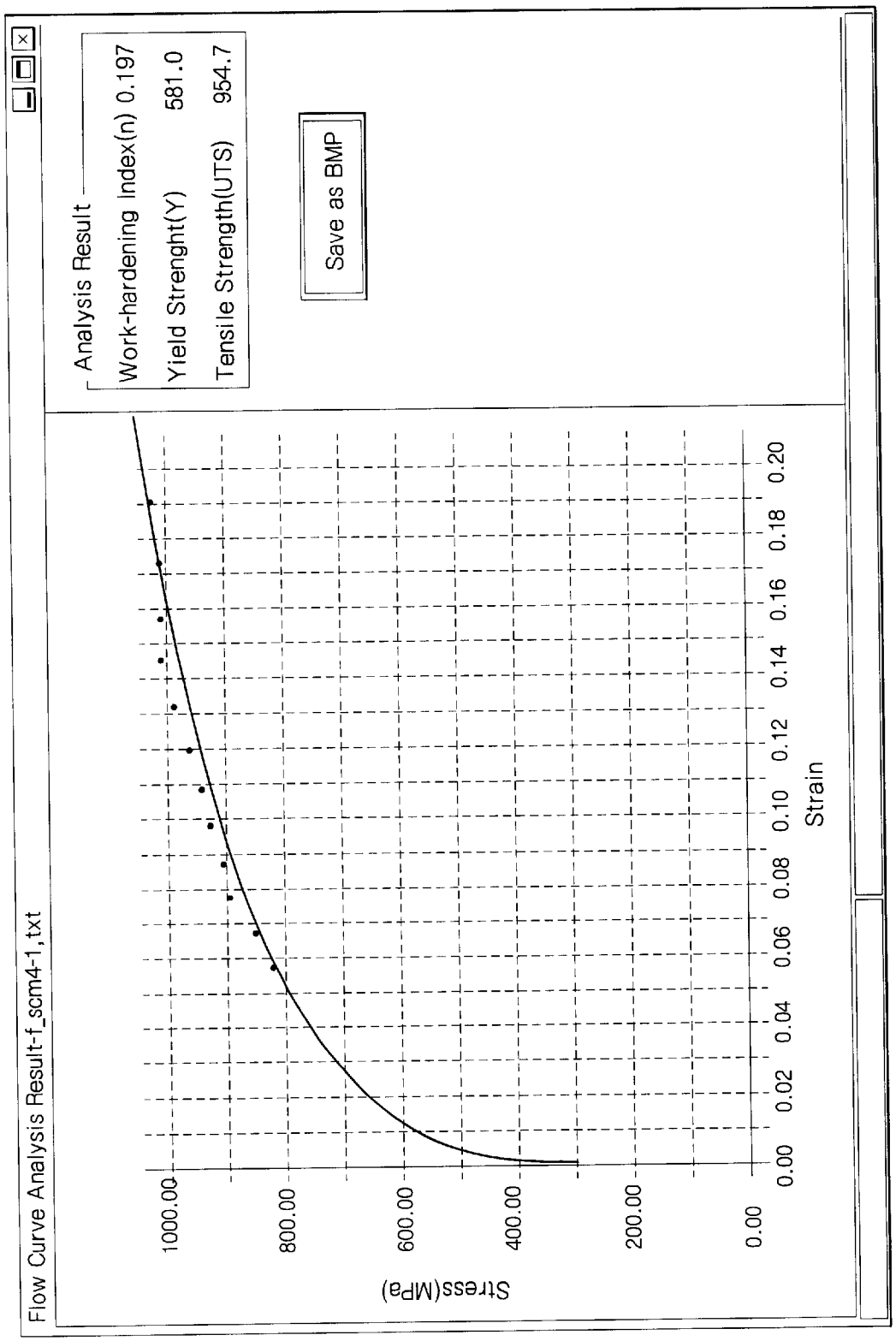

FIG. 9 is an initial picture of operation of programming means storing the method for measuring mechanical properties using the apparatus for indentation test. FIG. 10 is a picture of setting up the experiment condition. FIG. 11a is a picture of indentation load-displacement curve derived from the data measured by the apparatus for indentation test according to an embodiment of the present invention. FIG. 11b is a picture of indentation load-displacement curves derived by a number of testing of same or different materials. FIG. 12 is a flow curve derived from indentation load-displacement curve of FIG. 11a.

Referring to FIG. 9, the initial picture 400 operated by the computer comprises a function menu 410, a status of the apparatus 420, a manual operation of motor 430, an engage button 440, a graph window 450, a flow curve button 460, and a hardness analysis button 470. The elements of the initial picture can be operated by a mouse or a keyboard.

The function menu 410 includes a testing set up 410a, port set up 410b, and graph 410c, etc. FIG. 10, a picture of setting up the experiment condition is displayed by selecting testing set up menu 410a. The testing condition includes the kinds of indenter, the radius of indenter, times of multiple experiments, maximum displacement, unloading ratio, time of load holding, etc. The final depth(displacement) and the loading rate(rate of experiment) are controlled by manual set up menu at the bottom. The status of apparatus 420 displays load and displacement of the indenter 127 in the apparatus at present.

The manual operation of motor 430 is used to approach the indenter 127 to test materials or to withdraw the indenter 127 from test materials. Referring to FIG. 7, after setting of moving speed of the indenter(S120), pushing(S130) the 'Up' button of manual operation menu moves the indenter upward(S150). On the other hand, pushing the 'Down' button moves the indenter downward(S155).

The engage button 440 is for moving the indenter automatically to the appropriate position at which indentation test for test materials is possible before starting the test.

Pushing 'Start' button(not shown) starts to measure mechanical properties by operating the method stored in the programming means. The present load and displacement of the indenter are displayed in the status of apparatus. Also, indentation load curve at present state is displayed in the graph window 450 as is in FIG. 11A. FIG. 11B represents a few curves for comparing the change indentation load—indentation displacement according to the change of test points.

The initial picture 400 has a flow curve button 460 and a hardness analysis button 470. Pushing the flow curve button 460 displays a flow curve analysis window. Also pushing the hardness analysis button 470 displays hardness curve analysis window. Hardness number is derived by pushing analysis start button. For example, pushing the flow curve button 460 displays flow curve representing strain—stress relationship as in FIG. 12. Yield strength, tensile strength, strain-hardening coefficient are also displayed in FIG. 12. These data are saved in digital file such as BMP.

What is claimed is:

1. An apparatus for indentation test which measures load and displacement of test materials, comprising:

a load applying device comprising a AC servo motor, a reduction gear located below said motor and connected to said motor, a coupling located below said reduction gear and connected to said reduction gear, a connecting axis located below said coupling and connected to said coupling, bearings located around said connecting axis, and a ball screw located below said connecting axis, wherein said load applying device is adapted to transform power from said AC servo motor into a load applied to said test materials, said coupling being adapted to transport power generated by said motor to said connecting axis, said bearings supporting a the rotation movement of said connecting axis, and said ball screw being rotated by said power generated by said motor;

a load delivery device for transforming power generated by said load applying device to a vertical load for applying a load to said test materials, said load delivery device being compressively combined with a ball screw nut which in turn is combined with said ball screw whereby to create a supporting axis guiding said load delivery device in said load delivery device;

a load sensing device including a deformation gauge attached to said load delivery device by a screw for continuously measuring load applied to said test materials, wherein said load applied is performed by measuring a changed current due to a resistance change of said deformation gauge in proportion to a load applied to said test materials;

an extension axis located below said load sensing device in which a male screw located at an upper end of said extension axis is combined with a female screw located at a lower end of said load sensing device;

an indenting device located at an end of said extension axis and connected to said extension axis for applying a contact load to said test materials, said indenting device comprising an indenting device holder and an indenting tool combined as a single unit;

a displacement sensing device located below and parallel with said indenting device for measuring displacement of said indenting device;

a bracket attaching said extension axis which is connected to said indenting device via a connector which is connected to said displacement sensing device;

a horizontal moving device for moving a main body including said indenting device in a horizontal direction relative to a fixed main body base;

a main body base for supporting said main body; and a programming device connected to said main body for controlling said apparatus to advance said indenting device to a starting point to said test materials, apply a load to said test materials at a predetermined loading rate and for a predetermined indentation displacement, remove said load by moving said indenting device vertically upward according to a unloading ratio, measure indentation load and indentation displacement during load applying and load removing, repeating indentation load and indentation displacement measurements during repeated load applying and load removing cycles, removing said indenting device from said test materials, and drawing a indentation load-displacement curve based on said measurements.

2. The apparatus of claim 1, wherein said indenting device has a spherical, cone or square-pyramid shape in cross-section.

3. The apparatus of claim 1, wherein said displacement sensing device is adapted to be inserted into an inside groove formed at a lower end of said connector when force is applied, and to be restored to an initial position by elastic material that is installed in the inside groove when force is removed.

4. The apparatus of claim 1, wherein said horizontal moving device comprises a slider base which has a dovetail in an upper surface and is connected to said main body base at the upper surface of said slider base, a slider which is positioned between said slider base and said main body and has dovetail groove for attaching to the dovetail of said slider base at a lower surface, a screw groove made at a outer surface in the same direction with said dovetail groove, and a moving handle which has two ends, one end of which is screwed with a screw pitch of said screw groove of said slider, and the other end of which has a handle screwed with said remain body base or said slider base by a bracket.

5. The apparatus of claim 1, further comprising; an attaching device which is connected to said main body base to fix said apparatus to test materials, wherein said attaching device is selected from the group consisting of a magnet, a chain, and a U-block.

6. The apparatus of claim 1, further comprising;

a sensing device for controlling indenting device movement and for limiting movement of said indenting device for safety to avoid excessive upward or downward movement of said indenting device.

7. The apparatus of claim 1, wherein a maximum measurable displacement of said displacement sensing device is 2 mm.

8. The apparatus of claim 1, wherein said displacement sensing device comprises a LVDT (Linear Variable Displacement Transducer).

* * * * *

(12) EX PARTE REEXAMINATION CERTIFICATE (5744th)
United States Patent
Kwon et al.

(10) Number: US 6,718,820 C1
(45) Certificate Issued: Apr. 17, 2007

(54) APPARATUS FOR INDENTATION TEST AND METHOD FOR MEASURING MECHANICAL PROPERTIES USING IT

(75) Inventors: Dong-Il Kwon, Kangnam APT. #6-306, Bangbae 3-dong, Seocho-gu, Seoul (KR); Yeol Choi, Seoul (KR); Yun-hee Lee, Kyeongsangbuk-do (KR)

(73) Assignees: Frontics, Inc., Seoul (KR); Dong-Il Kwon, Seoul (KR)

Reexamination Request:
No. 90/007,214, Sep. 23, 2004

Reexamination Certificate for:
Patent No.: 6,718,820
Issued: Apr. 13, 2004
Appl. No.: 10/209,237
Filed: Jul. 31, 2002

(51) Int. Cl.
*G01N 3/48* (2006.01)

(52) U.S. Cl. .................. 73/81; 73/82; 73/83; 73/85; 73/87

(58) Field of Classification Search .................. None
See application file for complete search history.

(56) References Cited

U.S. PATENT DOCUMENTS 4,852,397 A 8/1989 Haggag

OTHER PUBLICATIONS

Haggag, F. M. "The Use of Field Indentation Microprobe in Measuring Mechanical Properties of Welds," *Proceedings of the 2nd International Conference on Trends in Welding Research*, May 1989, pp. 843–848, Gatlinburg, TN.

Haggag, F. M. "Application of Flow Properties Microprobe to Evaluate Gradients in Weldment Properties," *Proceedings of the 3rd International Conference on Trends in Welding Research*, Jun. 1992, p. 630, Gatlinburg, TN.

Haggag, F.M. "Use of Automated Ball Indentation Testing to Measure Flow Properties and Estimate Fracture Toughness in Metallic Materials," *Applications of Automation Technology to Fatigue and Fracture Testing*, 1990, pp. 189, 192, ASTM 1092, ASTM International, Philadelphia.

Haggag, F. M. "Computer Controlled Microindenter System," Final Report, DoD Contract No. N62269–95–C–0028, 1995, pp. 6,9, Naval Air Warfare Center, Patuxent River, MD.

*Primary Examiner*—Erik Kielin

(57) ABSTRACT

The present invention relates to an apparatus for indentation test, for measuring mechanical properties in the field. The present invention provides an apparatus which is suitable for measuring mechanical properties without compensative experimental constant for the analysis of measured data. The present invention provides an apparatus which is safe for testing the materials by utilizing a sensor for controlling indenter movement.

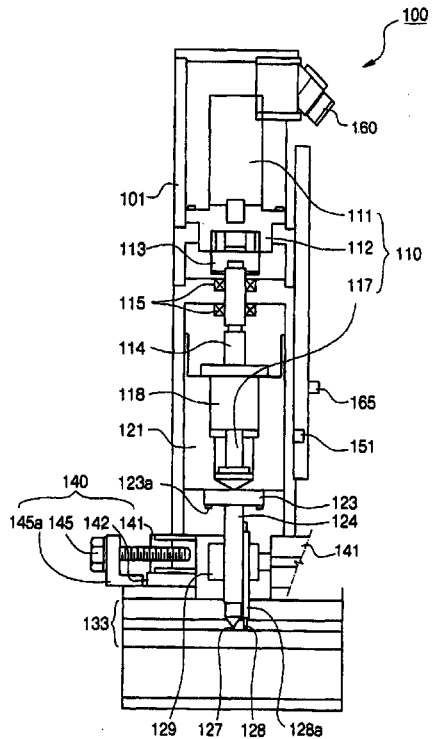

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–8 is confirmed.

* * * * *